(12) United States Patent
Schnabel et al.

(10) Patent No.: US 10,159,246 B2
(45) Date of Patent: Dec. 25, 2018

(54) COPOLYMERS OF N-VINYLCARBOXAMIDE AND DIALLYLDIALKYLAMMONIUM SALT AS DISPERSANT FOR AGROCHEMICAL FORMULATIONS

(75) Inventors: Gerhard Schnabel, Elsenfeld (DE); Ruth Wirschem, Mannheim (DE); Paul Klingelhoefer, Mannheim (DE); Lucelena Patricio Cardoso, Guaratingueta (BR)

(73) Assignee: BASF SE, Ludwigshafen (DE)

( * ) Notice: Subject to any disclaimer, the term of this patent is extended or adjusted under 35 U.S.C. 154(b) by 550 days.

(21) Appl. No.: 14/122,469

(22) PCT Filed: May 24, 2012

(86) PCT No.: PCT/EP2012/059778
§ 371 (c)(1),
(2), (4) Date: Nov. 26, 2013

(87) PCT Pub. No.: WO2012/163808
PCT Pub. Date: Dec. 6, 2012

(65) Prior Publication Data
US 2014/0080702 A1 Mar. 20, 2014

Related U.S. Application Data

(60) Provisional application No. 61/490,637, filed on May 27, 2011.

(30) Foreign Application Priority Data

May 27, 2011 (EP) ..................................... 11167952

(51) Int. Cl.
*A01N 25/10* (2006.01)
*A01N 43/56* (2006.01)
*C05G 3/02* (2006.01)
*A01N 25/04* (2006.01)
*A01N 25/30* (2006.01)
*A01N 47/24* (2006.01)

(52) U.S. Cl.
CPC ............. *A01N 25/10* (2013.01); *A01N 25/04* (2013.01); *A01N 25/30* (2013.01); *A01N 43/56* (2013.01); *A01N 47/24* (2013.01); *C05G 3/02* (2013.01)

(58) Field of Classification Search
CPC ........ A01N 47/24; A01N 57/20; A01N 25/04; A01N 25/30; A01N 2300/00; A01N 25/10; A01N 43/56; C05G 3/02
USPC .................................. 504/100, 101; 514/407
See application file for complete search history.

(56) References Cited

U.S. PATENT DOCUMENTS

| 2004/0170657 | A1 | 9/2004 | Morvan et al. | |
| 2006/0229209 | A1* | 10/2006 | Chrisstoffels | .......... A01N 25/10 504/361 |
| 2007/0225169 | A1* | 9/2007 | Hopkinson | ............ A01N 41/10 504/118 |
| 2008/0171658 | A1* | 7/2008 | Dyllick-Brenzinger | ..................... A01N 25/10 504/100 |
| 2011/0257016 | A1 | 10/2011 | Sowa et al. | |

FOREIGN PATENT DOCUMENTS

| EP | 0 069 573 | 4/1985 |
| EP | 0 808 568 | 11/1997 |
| JP | 7-252104 | 10/1995 |
| WO | WO 2004/050730 | 6/2004 |
| WO | WO 2008/076807 | 6/2008 |
| WO | WO 2010/072777 | 7/2010 |
| WO | WO 2010/093847 | 8/2010 |

OTHER PUBLICATIONS

International Search Report dated Oct. 11, 2012, prepared in International Application No. PCT/EP2012/059778.
International Preliminary Report on Patentability dated May 28, 2013, prepared in International Application No. PCT/EP2012/059778.
European Search Report dated Feb. 29, 2012, prepared in European Application No. 11 16 7952.
European Search Report dated Dec. 5, 2011, prepared in European Application No. 11 16 7952.
Innami, Harunori et al., "Herbicidal Composition containing polymers for preventing Herbicidal Incompatibility" (1995) Database—Chemical Abstracts Service—Accession No. 124:79451, European Search Report.

* cited by examiner

*Primary Examiner* — Johann R Richter
*Assistant Examiner* — Courtney A Brown
(74) *Attorney, Agent, or Firm* — Brinks Gilson & Lione

(57) ABSTRACT

The present invention relates to a composition comprising an agrochemical active substance and a copolymer which comprises an N-vinylcarboxamide and a diallyldialkylammonium salt incorporated into the polymer. The invention furthermore relates to a method of preparing this composition; to the use of this composition for dispersing agrochemical active substances; to a method of controlling phytopathogenic fungi and/or undesired plant growth and/or undesired insect or mite attack and/or for regulating the growth of plants, wherein the composition is allowed to act on the respective pests, their environment or the crop plants to be protected from the respective pest, on the soil and/or on undesired plants and/or on the crop plants and/or on their environment; and furthermore to seed comprising the composition.

16 Claims, No Drawings

COPOLYMERS OF N-VINYLCARBOXAMIDE AND DIALLYLDIALKYLAMMONIUM SALT AS DISPERSANT FOR AGROCHEMICAL FORMULATIONS

This application is a National Stage application of International Application No. PCT/EP2012/059778, filed May 24, 2012, which claims the benefit of U.S. Provisional Application No. 61/490,637, filed May 27, 2011, the entire contents of which are hereby incorporated herein by reference. This application also claims priority under 35 U.S.C. § 119 to European Patent Application No. 11167952.8, filed May 27, 2011, the entire contents of which is hereby incorporated herein by reference.

The present invention relates to a composition comprising an agrochemical active substance and a copolymer which comprises an N-vinylcarboxamide and a diallyldialkylammonium salt incorporated into the polymer. The invention furthermore relates to a process for the preparation of this composition; to the use of this composition for dispersing agrochemical active substances; to a method of controlling phytopathogenic fungi and/or undesired plant growth and/or undesired insect or mite attack and/or for regulating the growth of plants, wherein the composition is allowed to act on the respective pests, their environment or the plants to be protected from the respective pest, on the soil and/or on undesired plants and/or on the crop plants and/or their environment; and furthermore to seed comprising the composition. The present invention comprises combinations of preferred features with other preferred features.

A wide range of polymers are known as adjuvants for agricultural formulations:

EP 0 808 568 discloses a multilayer intercalated system incorporating pesticides and a water-soluble polymer. A suitable one is polyquaternium-6, a poly(diallyldimethylammonium chloride).

US 2004/0170657 discloses an aqueous emulsion, the aqueous phase comprising a salt of a crop protection agent, and an amphiphilic block polymer. The hydrophilic block of the block polymer may be constructed of diallyldialkylammonium salt.

Disadvantages of the prior art are, inter alia, that no high storage stability of the formulation is achieved; that the particle size growth of dispersed agrochemical active substances is not slowed down or suppressed; that the agglomeration of dispersed agrochemical active substances is not slowed down or suppressed; that the settling of dispersed agrochemical active substances is not slowed down or suppressed; and that abovementioned advantages manifest themselves in particular in the presence of high salt concentrations. It was therefore an object to overcome these disadvantages.

The object was achieved by a composition comprising an agrochemical active substance and a copolymer which comprises an N-vinylcarboxamide and a diallyldialkylammonium salt incorporated into the polymer.

The copolymer is preferably a random copolymer. The term "random" usually means that the incorporation of at least two different monomers into the resulting polymer is randomly distributed. Usually, the random copolymer is a free-radical polymer, in other words a polymer prepared from monomers by free-radical polymerization.

Preferred diallyldialkylammonium salts conform to the formula (I)

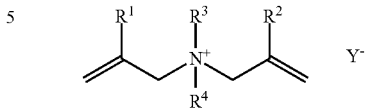

where $R^1$ and $R^2$ independently of one another are hydrogen or $C_1$-$C_4$-alkyl; $R^3$ and $R^4$ independently of one another are alkyl, hydroxyalkyl, carboxyalkyl, carboxyamidoalkyl or alkoxyalkyl having 1 to 18 carbon atoms; and Y is an anion. With preference, $R^1$ and $R^2$ independently of one another are hydrogen or methyl, more particularly hydrogen. With preference, $R^3$ and $R^4$ independently of one another are $C_1$-$C_{18}$-alkyl, more preferably $C_1$-$C_6$-alkyl, and more particularly methyl. Y is preferably a halide (such as chloride, bromide), a sulfate or a phosphate.

Particularly preferred diallyldialkylammonium salts are diallyldimethylammonium chloride (DADMAC), diallyldimethylammonium bromide, diallyldimethylammonium sulfate, diallyldimethylammonium phosphate, dimethallyldimethylammonium chlorides, diethallyldimethylammonium chloride, diallyldi(beta-hydroxyethyl)ammonium chloride, and diallyldi(beta-ethoxyethyl)ammonium chloride, and also mixtures thereof. An especially preferred diallyldialkylammonium salt is DADMAC.

The copolymer may contain up to 90% by weight, preferably up to 60% by weight, and more preferably up to 40% by weight of diallyldialkylammonium salt. The copolymer may comprise at least 1% by weight, preferably at least 5% by weight, and more preferably at least 15% by weight of diallyldialkylammonium salts. The copolymer can comprise 1 to 70% by weight, preferably 5 to 50% by weight, and more preferably 10 to 30% by weight of diallyldialkylammonium salt. The figures in % by weight here are based in each case on the total amount of the copolymerized monomers.

Preferred N-vinylcarboxamides are N-vinyl-$C_1$-$C_{18}$-alkylcarboxamides and/or N-vinyl-N—($C_1$-$C_{12}$-alkyl)-$C_1$-$C_{18}$-alkylcarboxamides. Particularly preferred N-vinylcarboxamides are N-vinyl-$C_1$-$C_4$-alkylcarboxamides and N-vinyl-N—($C_1$-$C_4$-alkyl)-$C_1$-$C_4$-alkylcarboxamides, with the N-vinyl-$C_1$-$C_4$-alkylcarboxamides being better suited.

Particularly good N-vinylcarboxamides are N-vinyl-N-methylformamide, N-vinylformamide, N-vinyl-N-ethylformamide, N-vinyl-N-propylformamide, N-vinyl-N-isopropylformamide, N-vinyl-N-isobutylformamide, N-vinylacetamide, N-vinyl-N-methylacetamide, N-vinylpropionamide, or N-vinyl-N-methylpropionamide, and also mixtures thereof. The most suitable N-vinyl-carboxamide is N-vinylformamide.

The copolymer may comprise up to 95% by weight, and preferably up to 90% by weight, of N-vinylcarboxamide. The copolymer may comprise at least 5% by weight, preferably at least 20% by weight, more preferably at least 30% by weight, and especially at least 50% by weight of N-vinylcarboxamide. The copolymer may comprise 20 to 95% by weight, preferably 40 to 95% by weight, and more preferably 60 to 95% by weight of N-vinylcarboxamide. The figures in % by weight here are based in each case on the total amount of the copolymerized monomers.

In one particularly preferred form, the copolymer (preferably in random form) comprises in copolymerized form an N-vinyl-$C_1$-$C_4$-alkylcarboxamide and a diallyldialkylammonium salt of the formula (I) in which $R^1$ and $R^2$ are hydrogen. Stated by way of example is the copolymer of the formula (II),

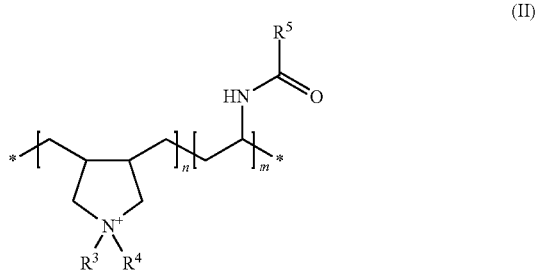

(II)

where $R^3$ and $R^4$ independently of one another are $C_1$-$C_{18}$-alkyl, more preferably $C_1$-$C_6$-alkyl, and more particularly methyl; and $R^5$ is H or $C_1$-$C_6$-alkyl or $C_1$-$C_6$-alkoxy, preferably H or $C_1$-$C_6$-alkyl, and more particularly H.

In an especially preferred form, the copolymer (preferably in random form) comprises, in copolymerized form, an N-vinyl-$C_1$-$C_4$-alkylcarboxamide and a diallyldialkylammonium salt of formula (I) in which $R^1$ and $R^2$ are hydrogen.

The copolymer may comprise up to 100% by weight, preferably up to 90% by weight and more preferably up to 80% by weight of the sum of diallyldialkylammonium salt and N-vinylcarboxamide. The copolymer may comprise at least 30% by weight, preferably at least 60% by weight, and more preferably at least 90% by weight of the sum of diallyldialkylammonium salt and N-vinylcarboxamide. The figures in % by weight here are based in each case on the total amount of the copolymerized monomers.

The copolymer may comprise further monomers in copolymerized form. Further monomers which may be present are, for example, vinylaromatic monomers such as styrene and styrene derivatives, such as α-methylstyrene, vinyltoluene, ortho-, meta- and para-methylstyrene, ethylvinylbenzene, vinylnaphthalene, vinylxylene and the corresponding halogenated vinylaromatic monomers, vinylaromatic monomers which bear nitro, alkoxy, haloalkyl, carbalkoxy, carboxy, amino and alkylamino groups, α-olefins, such as ethene, propene, 1-butene, 1-pentene, 1-hexene, isobutene, long-chain (C10-C20)-alkyl-α-olefins, dienes such as butadiene and isoprene, vinyl alcohol esters such as vinyl acetate, vinyl halides such as vinyl chloride, vinyl bromide, vinyl fluoride, vinylidene chloride, vinylidene fluoride, vinylidene bromide, vinylnitrile, vinyl carboxylates, 1-vinylamides such as 1-vinylpyrrolidone, 1-vinylpiperidone, 1-vinylcaprolactam, N-vinylimidazole, $C_1$-$C_{24}$-alkylesters and monosubstituted and disubstituted and unsubstituted $C_1$- to $C_{24}$-alkylamides of monoethylenically unsaturated monomers such as acrylic acid, methacrylic acid, fumaric acid, maleic acid and itaconic acid, vinylsulfonic acid, anhydrides such as maleic anhydride, unsaturated aldehydes such as acrolein, unsaturated ethers such as 1,4-cyclohexanedimethanol divinyl ether, 1,4-cyclohexanedimethanol monovinyl ether, butanediol divinyl ether, butanediol monovinyl ether, cyclohexyl vinyl ether, diethylene glycol divinyl ether, ethylene glycol monovinyl ether, ethyl vinyl ether, methyl vinyl ether, n-butyl vinyl ether, octadecyl vinyl ether, triethylene glycol vinyl methyl ether, vinyl isobutyl ether, vinyl 2-ethylhexyl ether, vinyl propyl ether, vinyl isopropyl ether, vinyl dodecyl ether, vinyl tert.-butyl ether, hexandiol divinyl ether, hexandiol monovinyl ether, diethylene glycol monovinyl ether, diethylaminoethyl vinyl ether, polytetrahydrofuran-290 divinyl ether, tetraethylene glycol divinyl ether, triallylamine, ethylene glycol butyl vinyl ether, ethylene glycol divinyl ether, triethylene glycol divinyl ether, trimethylolpropane trivinyl ether, aminopropyl vinyl ether. Preferred further monomers are those having at least two olefinically unsaturated double bonds, such as triallylamine.

In another form the further monomers are essentially free (e.g. contained in up to 5 wt %, preferably up to 1 wt %) of an ester of an ethylenically unsaturated carboxylic acid, wherein the carboxylic acid ester exhibits alkoxylate residues of the general formula (A)

in which $R^a$ is hydrogen or an aliphatic hydrocarbon residue with 3 to 40 carbon atoms; $R^b$, $R^c$, $R^d$ are, independently of one another, hydrogen or $C_{1-4}$-alkyl; w, x, z correspond, independently of one another, to a value of 0 to 100, the sum of w, x and z being greater than 0; y corresponds to a value of 1 to 20; X is N or O, n being 1 and $R^a$ not being hydrogen if X is O; or n being 2 if X is N.

Copolymers which comprise in copolymerized form an N-vinylcarboxamide and a diallyldialkylammonium salt, and their preparation, are general knowledge, as for example from Tanaka et al., J. Appl. Polymer Sci. 2007, 104, 1068-1075, WO 2004/058831 or EP 1 059 316.

The copolymer is usually synthesized in the usual manner by means of free-radical polymerization. However, it is also possible to employ other processes for the polymerization, for example controlled free-radical processes. The polymerization is carried out in the presence of the monomers and of one or more initiators and can be carried out with or without solvent, in emulsion or in suspension. The polymerization can be carried out as a batch reaction, as a semicontinuous operation or as a continuous operation. The reaction times are generally in the range of between 1 and 12 hours. The temperature range within which the reactions can be carried out is generally from 20 to 200° C., preferably from 40 to 120° C.

The initiators which are employed for the free-radical polymerization are customary free-radical-forming substances. The initiator is preferably selected from the group of the azo compounds, of the peroxide compounds or of the hydroperoxide compounds. Examples that may be stated include acetyl peroxide, benzoyl peroxide, lauroyl peroxide, tert.-butyl peroxyisobutyrate, caproyl peroxide, cumene hydroperoxide, azobisisobutyronitrile or 2,2-azobis(2-methylbutane)nitrile. Particularly preferred is azobisisobutyronitrile (AIBN).

The free-radical polymerization is preferably carried out in solution. Solvents are water, alcohols such as, for example, methanol, ethanol, propanol, dipolar-aprotic solvents such as, for example, DMF, DMSO or NMP, aromatic, aliphatic, halogenated or nonhalogenated hydrocarbons such as, for example, hexane, chlorobenzene, toluene or benzene. Preferred solvents are water, isopropanol, methanol, toluene, DMF, NMP, DMSO and hexane.

The molar mass Mw of the copolymer is usually in the range of from 500 to 250 000 g/mol, preferably from 5000 to 250 000 g/mol, especially preferably at from 20 000 to 220 000 g/mol and in particular at from 60 000 to 200 000 g/mol. The molar masses Mw and Mn and the polydispersity of the polymers are determined by size-exclusion chromatography. Commercially available PMMA-standard units may be used as the calibration material.

The copolymer is usually soluble in water, for example to at least 5 g/l at 20° C. (preferably to at least 20 g/l, in particular at least 50 g/l). The terpolymer is preferably present in dissolved form in the composition according to the invention.

The composition according to the invention usually comprises at least 0.1% by weight, preferably at least 1% by weight and in particular at least 2% by weight of the copolymer. The composition according to the invention usually comprises from 0.1 to 25% by weight, preferably from 0.5 to 15% by weight and in particular from 1 to 10% by weight of the copolymer.

Suitable agrochemical active substances are pesticides and inorganic fertilizers.

The term pesticides refers to at least one active substance selected from the group of the fungicides, insecticides, nematicides, herbicides, safeners and/or growth regulators. Preferred pesticides are fungicides, insecticides, herbicides and growth regulators. Especially preferred pesticides are herbicides. Mixtures of pesticides from two or more of the abovementioned classes may also be used. The skilled worker is familiar with such pesticides, which can be found, for example, in Pesticide Manual, 15th Ed. (2009), The British Crop Protection Council, London. The following pesticides are suitable, by way of example (pesticides A) to K) are fungicides):

A) Respiration Inhibitors
complex-III-inhibitors at the $Q_o$-site (for example strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, methyl 2-[2-(2,5-dimethylphenyloxymethyl)phenyl]-3-methoxyacrylate, 2-(2-(3-(2,6-dichlorophenyl)-1-methylallylideneaminooxymethyl)phenyl)-2-methoxyimino-N-methylacetamide, pyribencarb, triclopyricarb/chlorodincarb, famoxadon, fenamidon;
complex-III-inhibitors at the $Q_i$-site: cyazofamid, amisulbrom;
complex-II-inhibitors (for example carboxamides): benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthio-biphenyl-2-yl)-3-difluoromethyl-1-methyl-1H-pyrazole-4-carboxamide, N-(2-(1,3,3-trimethylbutyl)phenyl)-1,3-dimethyl-5-fluoro-1H-pyrazole-4-carboxamide and N-[9-(dichloromethylene)-1,2,3,4-tetrahydro-1,4-methanonaphthalen-5-yl]-3-(difluoromethyl)-1-methyl-1H-pyrazole-4-carboxamide;
other respiration inhibitors (for example complex I, decouplers): diflumetorim; nitrophenyl derivatives: binapacryl, dinobuton, dinocap, fluazinam; ferimzone; organometal compounds: fentin salts such as fentin acetate, fentin chloride or fentine hydroxide; ametoctradin; and silthiofam;

B) Sterol Biosynthesis Inhibitors (SBI Fungicides)
C14-demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole;
imidazoles: imazalil, pefurazoate, prochloraz, triflumizole; pyrimidines, pyridines and piperazines: fenarimol, nuarimol, pyrifenox, triforine;
delta14-reductase inhibitors: aldimorph, dodemorph, dodemorph acetate, fenpropimorph, tridemorph, fenpropidin, piperalin, spiroxamine;
3-ketoreductase inhibitors: fenhexamid;

C) Nucleic Acid Synthesis Inhibitors
phenylamides or acylamino acid fungicides: benalaxyl, benalaxyl-m, kiralaxyl, metalaxyl, metalaxyl-M (mefenoxam), ofurace, oxadixyl;
others: hymexazole, octhilinone, oxolinic acid, bupirimate;

D) Cell Division and Cytoskeleton Inhibitors
tubulin inhibitors such as benzimidazoles, thiophanates: benomyl, carbendazim, fuberidazole, thiabendazole, thiophanate-methyl; triazolopyrimidines: 5-chloro-7-(4-methyl-piperidin-1-yl)-6-(2,4,6-trifluorophenyl)-[1,2,4]triazolo[1,5-a]pyrimidine;
further cell division inhibitors: diethofencarb, ethaboxam, pencycuron, fluopicolid, zoxamid, metrafenon, pyriofenon;

E) Amino Acid Synthesis and Protein Synthesis Inhibitors
methionine synthesis inhibitors (anilinopyrimidines): cyprodinil, mepanipyrim, pyrimethanil;
protein synthesis inhibitors: blasticidin-S, kasugamycin, kasugamycin hydrochloride hydrate, mildiomycin, streptomycin, oxytetracyclin, polyoxin, validamycin A;

F) Signal Transduction Inhibitors
MAP/histidine kinase inhibitors: fluoroimide, iprodione, procymidone, vinclozolin, fenpiclonil, fludioxonil;
G-protein inhibitors: quinoxyfen;

G) Lipid and Membrane Synthesis Inhibitors
phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall attachment: dimethomorph, flumorph, mandipropamid, pyrimorph, benthiavalicarb, iprovalicarb, valifenalate and 4-fluorophenyl N-(1-(1-(4-cyanophenyl)ethanesulfonyl)but-2-yl)carbamate;
compounds which affect cell membrane permeability and fatty acids: propamocarb, propamocarb hydrochloride H) "Multi-Site" Inhibitors
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (for example phthalimides, sulfamides, chloronitriles): anilazine, chlorothalonil, captafol, captan, folpet, dichlofluanid, dichlorophen, flusulfamide, hexachlorobenzene, pentachlorophenol and its salts, phthalid, tolylfluanid, N-(4-chloro-2-nitrophenyl)-N-ethyl-4-methylbenzenesulfonamide;
guanidines and others: guanidine, dodine, dodine-free base, guazatin, guazatin acetate, iminoctadin, iminoctadin triacetate, iminoctadin tris(albesilate), dithianon;

I) Cell Wall Biosynthesis Inhibitors
glucan synthesis inhibitors: validamycin, polyoxin B;
melanin synthesis inhibitors: pyroquilon, tricyclazole, carpropamid, dicyclomet, fenoxanil;

J) Resistance Inductors
acibenzolar-S-methyl, probenazol, isotianil, tiadinil, prohexadione-calcium; phosphonates: fosetyl, fosetyl-aluminum, phosphorous acid and its salts;

K) Unknown Mode of Action bronopol, quinomethionate, cyflufenamid, cymoxanil, dazomet, debacarb, diclomezin, difenzoquat, difenzoquat-methyl sulfate, diphenylamine, fenpyrazamine, flumetover, flusulfamid, flutianil, methasulfocarb, nitrapyrin, nitrothal-isopropyl, oxine-copper, proquinazid, tebufloquin, tecloftalam, triazoxide, 2-butoxy-6-iodo-3-propylchromene-4-one, N-(cyclopropyl-methoxyimino-(6-difluoromethoxy-2,3-difluorophenyl)methyl)-2-phenyl-acetamide, N'-(4-(4-chloro-3-trifluoromethylphenoxy)-2,5-dimethylphenyl)-N-ethyl-N-methylformamidine, N'-(4-(4-fluoro-3-trifluoromethylphenoxy)-2,5-dimethylphenyl)-N-ethyl-N-methylformamidine, N'-(2-methyl-5-trifluoromethyl-4-(3-trimethylsilanylpropoxy)phenyl)-N-ethyl-N-methylformamidine, N'-(5-difluoromethyl-2-methyl-4-(3-trimethylsilanylpropoxy)-phenyl)-N-ethyl-N-methylformamidine, N-methyl-(1,2,3,4-tetrahydronaphthalen-1-yl)-2-{1-[2-(5-methyl-3-trifluoromethylpyrazol-1-yl)acetyl]piperidin-4-yl}thiazole-4-carboxamide, N-methyl-(R)-1,2,3,4-tetrahydronaphthalen-1-yl 2-{1-[2-(5-methyl-3-trifluoromethylpyrazol-1-yl)-acetyl]piperidin-4-yl}thiazole-4-carboxamide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, 6-tert.-butyl-8-fluoro-2,3-dimethylquinolin-4-yl methoxyacetate, N-methyl-2-{1-[(5-methyl-3-trifluoromethyl-1H-pyrazol-1-yl)acetyl]piperidin-4-yl}-N-[(1R)-1,2,3,4-tetrahydronaphthalen-1-yl]-4-thiazole-carboxamide, 3-[5-(4-methylphenyl)-2,3-dimethylisoxazolidin-3-yl]-pyridine, 3-[5-(4-chlorophenyl)-2,3-dimethylisoxazolidin-3-yl]-pyridine (pyrisoxazol), N-(6-methoxypyridin-3-yl) cyclopropanecarboxamide, 5-chloro-1-(4,6-dimethoxypyrimidin-2-yl)-2-methyl-1H-benzoimidazole, 2-(4-chlorophenyl)-N-[4-(3,4-dimethoxyphenyl)isoxazol-5-yl]-2-prop-2-ynyloxyacetamide;

M) Growth Regulators abscisic acid, amidochlor, ancymidole, 6-benzylaminopurine, brassinolide, butralin, chlormequat (chlormequat chloride), choline chloride, cyclanilid, daminozide, dikegulac, dimethipin, 2,6-dimethylpuridine, ethephon, flumetralin, flurprimidol, fluthiacet, forchlorfenuron, gibberellic acid, inabenfid, indole-3-acetic acid, maleic hydrazide, mefluidid, mepiquat (mepiquat chloride), metconazole, naphthaleneacetic acid, N-6-benzyladenine, paclobutrazole, prohexadione (prohexadione-calcium), prohydrojasmone, thidiazuron, triapenthenol, tributylphosphorotrithioate, 2,3,5-triiodobenzoic acid, trinexapac-ethyl and uniconazole;

N) Herbicides acetamides: acetochlor, alachlor, butachlor, dimethachlor, dimethenamid, flufenacet, mefenacet, metolachlor, metazachlor, napropamid, naproanilid, pethoxamid, pretilachlor, propachlor, thenylchlor;

amino acid analogs: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

bipyridyls: diquat, paraquat;

carbamates and thiocarbamates: asulam, butylate, carbetamide, desmedipham, dimepiperat, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bromoxynil, dichlobenil, ioxynil;

imidazolinones: imazamethabenz, imazamox, imazapic, imazapyr, imazaquin, imazethapyr;

phenoxyacetic acids: clomeprop, 2,4-dichlorophenoxy-acetic acid (2,4-D), 2,4-DB, dichlorprop, MCPA, MCPA-thioethyl, MCPB, mecoprop;

pyrazines: chloridazon, flufenpyr-ethyl, fluthiacet, norflurazon, pyridate;

pyridines: aminopyralid, clopyralid, diflufenican, dithiopyr, fluridone, fluroxypyr, picloram, picolinafen, thiazopyr;

sulfonylureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propylimidazo[1,2-b]pyridazin-3-yl)sulfonyl)-3-(4,6-dimethoxypyrimidin-2-yl)urea;

triazines: ametryne, atrazine, cyanazine, dimethametryne, ethiozine, hexazinone, metamitron, metribuzine, prometryne, simazine, terbuthylazine, terbutryne, triaziflam;

ureas: chlortoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, orthosulfamuron, penoxsulam, propoxycarbazone, pyribambenz-propyl, pyribenzoxim, pyriftalide, pyriminobac-methyl, pyrimisulfan, pyrithiobac, pyroxasulfon, pyroxsulam;

others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethyl, chlorthal, cinmethylin, clomazone, cumyluron, cyprosulfamid, dicamba, difenzoquat, diflufenzopyr, *Drechslera monoceras*, endothal, ethofumesate, etobenzanid, fentrazamide, flumiclorac-pentyl, flumioxazin, flupoxam, fluorochloridon, flurtamon, indanofan, isoxaben, isoxaflutol, lenacil, propanil, propyzamide, quinclorac, quinmerac, mesotrione, methylarsenic acid, naptalam, oxadiargyl, oxadiazone, oxaziclomefon, pentoxazone, pinoxaden, pyraclonil, pyraflufen-ethyl, pyrasulfotol, pyrazoxyfen, pyrazolynate, quinoclamin, saflufenacil, sulcotrione, sulfentrazone, terbacil, tefuryltrione, tembotrione, thiencarbazone, topramezone, 4-hydroxy-3-[2-(2-methoxyethoxy-methyl)-6-trifluoromethylpyridin-3-carbonyl]bicyclo[3.2.1]oct-3-en-2-one, ethyl (3-[2-chloro-4-fluoro-5-(3-methyl-2,6-dioxo-4-trifluoromethyl-3,6-dihydro-2H-pyrimidin-1-yl) phenoxy]pyridin-2-yloxy)acetate, methyl 6-amino-5-chloro-2-cyclopropylpyrimidine-4-carboxylate, 6-chloro-3-(2-cyclopropyl-6-methylphenoxy) pyridazin-4-ol, 4-amino-3-chloro-6-(4-chlorophenyl)-

5-fluoropyridin-2-carboxylic acid, methyl 4-amino-3-chloro-6-(4-chloro-2-fluoro-3-methoxy-phenyl)pyridin-2-carboxylate and methyl 4-amino-3-chloro-6-(4-chloro-3-dimethylamino-2-fluorophenyl)pyridin-2-carboxylate;

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin, insect growth inhibitors: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazin; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramate;

nicotine receptor agonists/antagonists: clothianidin, dinotefuran, imidacloprid, thiamethoxam, nitenpyram, acetamiprid, thiacloprid, 1-(2-chlorothiazol-5-ylmethyl)-2-nitrimino-3,5-dimethyl-[1,3,5]triazinane;

GABA antagonists: endosulfan, ethiprole, fipronil, vaniliprole, pyrafluprole, pyriprole, N-5-amino-1-(2,6-dichloro-4-methylphenyl)-4-sulfinamoyl-1H-pyrazole-3-thiocarboxamide;

macrocyclic lactones: abamectin, emamectin, milbemectin, lepimectin, spinosad, spinetoram;

mitochondrial electron transport chain inhibitor (METI) I acaricides: fenazaquin, pyridaben, tebufenpyrad, tolfenpyrad, flufenerim;

METI II and III substances: acequinocyl, fluacyprim, hydramethylnone;

decouplers: chlorfenapyr;

inhibitors of oxidative phosphorylation: cyhexatin, diafenthiuron, fenbutatin oxide, propargite;

insect ecdysis inhibitors: cryomazine;

'mixed function oxidase' inhibitors: piperonyl butoxide;

sodium channel blockers: indoxacarb, metaflumizone;

others: benclothiaz, bifenazate, cartap, flonicamid, pyridalyl, pymetrozin, sulfur, thiocyclam, flubendiamide, chlorantraniliprole, cyazypyr (HGW86); cyenopyrafen, flupyrazofos, cyflumetofen, amidoflumet, imicyafos, bistrifluoron and pyrifluquinazone.

Examples of inorganic fertilizers are customary fertilizer components, nitrogen sources which may be used being, for example, ammonium sulfate, ammonium nitrate, ammonium chloride, ammonia sulfa-nitrate, urea, cyanamide, dicyandiamide, sodium nitrate, Chile saltpetre or calcium nitrate, and slow-release fertilizers such as oxamide, urea/formaldehyde condensates, urea/acetaldehyde condensates or urea/glyoxal condensates, for example Ureaform, acetylene diurea, isobutylidene diurea or crotonylidene diurea. Compounds which comprise one or more of the plant nutrients phosphorus, potassium, magnesium, calcium or sulfur, and compounds which comprise the trace elements boron, iron, copper, zinc, manganese or molybdenum, may also be present. Examples of such compounds are monoammonium phosphate, diammonium phosphate, superphosphate, Thomas meal, triple superphosphate, dicalcium phosphate, potassium phosphate, partially or fully digested crude phosphates, potassium nitrate, potassium chloride, potassium sulfate, dipotassium phosphate, magnesium sulfate, magnesium chloride, kieserite, dolomite, chalk, colemanite, boric acid, borax, iron sulfate, copper sulfate, zinc sulfate, manganese sulfate, ammonium molybdate or similar substances.

Preferably, the agrochemical active substance comprises a water-insoluble first pesticide. The first pesticide will in most cases be soluble in water to no more than 10 g/l at 20° C., preferably to no more than 1 g/l and in particular to no more than 0.5 g/l. The skilled worker can simply select pesticides with a suitable solubility from the above pesticide list.

The water-insoluble pesticide usually has a boiling point of above 30° C., preferably above 40° C. and specifically above 45° C.

Preferred water-insoluble first pesticides are saflufenacil, dimethenamid-p, pendimethalin, picolinafen, pyraclostrobin, fipronil, metaflumizon, water-insoluble azole fungicides and water-insoluble auxin esters (such as alkyl esters of 2,4-D, for example the 2-ethylhexyl, isobutyl, isooctyl ester of 2,4-D). Water-insoluble azole fungicides can, depending on the desired solubility, be selected among triazoles (such as azaconazole, bitertanol, bromuconazole, cyproconazole, difenoconazole, dini-conazole, diniconazole-M, epoxiconazole, fenbuconazole, fluquinconazole, flusilazol, flutriafol, hexaconazole, imibenconazole, ipconazole, metconazole, myclobutanil, oxpoconazole, paclobutrazol, penconazole, propiconazole, prothioconazole, simeconazole, tebuconazole, tetraconazole, triadimefon, triadimenol, triticonazole, uniconazole); imidazoles (such as cyazofamid, imazalil, imazalil sulfate, pefurazoate, prochloraz, triflumizole); benzimidazoles: benomyl, carbendazim, fuberidazole, thiabendazole; or other azoles (such as ethaboxam, etridiazole, hymexazole, 2-(4-chlorophenyl)-N-[4-(3,4-dimethoxyphenyl)isoxazol-5-yl]-2-prop-2-ynyloxy-acetamid), with the triazoles being preferred.

The agrochemical active substance especially preferably comprises a) a water-insoluble first pesticide and b) a water-soluble second pesticide or a water-soluble inorganic fertilizer.

The water-soluble second pesticide will in most cases be soluble in water to more than 10 g/l at 20° C. Preferably, it is soluble in water to more than 50 g/l, in particular more than 100 g/l. The skilled worker can simply select pesticides with a suitable solubility from the above pesticide list. The second pesticide is preferably a herbicide and/or a growth regulator, with herbicides being especially preferred. Mixtures of different water-soluble salts of a second pesticide are likewise possible.

Preferred water-soluble second pesticides are glyphosate, glufosinate, 2,4-D, dicamba, paraquat, diquat, chlormequat and mepiquat. Preferred second pesticides are glyphosate (for example as the free acid, the sodium salt, the sesquisodium salt, the potassium salt, the dipotassium salt, the ammonium salt, the diammonium salt, the dimethyl ammonium salt, the trimesium salt or the isopropylamine salt), glufosinate (for example as the ammonium salt), 2,4-D (for example as the ammonium, $C_1$-$C_{12}$-alkylammonium or sodium salt) and dicamba (for example as the diglycolamine, dimethylammonium, diolamine, olamine, potassium, sodium, trolamine salt). The second pesticide especially preferably comprises glyphosate (for example as the potassium salt, ammonium salt, isopropylamine salt).

The water-soluble inorganic fertilizer is in most cases soluble in water to more 10 g/l at 20° C. Preferably, it is soluble in water to more than 50 g/l, in particular more than 100 g/l. The skilled worker can simply select fertilizers with a suitable solubility from the above fertilizer list. Preferred inorganic fertilizers are sulfates, phosphates or nitrates, in particular ammonium sulfate, ammonium nitrate, and/or ammonium phosphate.

The composition according to the invention usually comprises from 0.5 to 99% by weight, preferably 5 to 85% by weight and in particular 15 to 70% by weight of agrochemical active substances such as pesticides and/or inorganic fertilizers.

The composition according to the invention usually comprises from 0.5 to 70% by weight, preferably 1 to 50% by weight and in particular 1 to 30% by weight water-insoluble first pesticide.

The composition according to the invention normally comprises at least 5% by weight, preferably at least 10% by weight, and in particular at least 20% by weight of the water-soluble second pesticide or of the water-soluble, inorganic fertilizer. The composition according to the invention normally comprises 1 to 80% by weight, preferably 5 to 65% by weight, and in particular 15 to 45% by weight of the water-soluble second pesticide or of the water-soluble, inorganic fertilizer.

The weight ratio of water-insoluble first pesticide to copolymer can vary within any range, for example in the range of from 1:10 000 to 10 000:1, preferably in the range of from 1:1000 to 1000:1, especially preferably in the range of from 1:100 to 100:1.

The composition according to the invention is preferably present in the form of an agrochemical composition. Usual types of agrochemical compositions are, for example, solutions, emulsions, suspensions, dusts, powders, pastes and granules. Examples of types of compositions here are suspensions (SC, OD, FS), emulsifiable concentrates (EC), emulsions (EW, EO, ES), pastes, pills, wettable powders or dusts (WP, SP, SS, WS, DP, DS) or granules (GR, FG, GG, MG), which can either be soluble or dispersible (wettable) in water, and gels for the treatment of plant propagation materials such as seed (GF). The agrochemical compositions are prepared in the known manner (see for example Mollet, H. and Grubemann, A.: Formulation technology (Wiley VCH Verlag, Weinheim, 2001)).

The agrochemical compositions can furthermore also comprise conventional adjuvants which are conventionally used for plant protection products, the choice of the adjuvants depending on the specific use form or the active substance. Examples of suitable adjuvants are solvents, solid carriers, surface-active substances (such as further solubilizers, protective colloids, wetters and adhesives), organic and inorganic thickeners, bactericides, antifreeze agents, antifoams, optionally colorants and stickers (for example for the treatment of seed).

Suitable solvents are water, organic solvents such as mineral oil fractions of medium to high boiling point such as kerosene, and diesel oil, furthermore coal tar oils and oils of vegetable or animal origin, aliphatic, cyclic and aromatic hydrocarbons, for example paraffins, tetrahydro-naphthalene, alkylated naphthalenes and their derivatives, alkylated benzenes and their derivatives, alcohols such as methanol, ethanol, propanol, butanol and cyclohexanol, glycols, ketones such as cyclohexanone, gamma-butyrolactone, dimethyl fatty acid amides, fatty acids and fatty acid esters and strongly polar solvents, for example amines such as N-methyl-pyrrolidone. In principle, it is also possible to use solvent mixtures and mixtures of the abovementioned solvents and water.

Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders or other solid carriers.

Suitable surface-active substances (adjuvants, wetters, adhesives, dispersants or emulsifiers) are the alkali, alkaline-earth, ammonium salts of aromatic sulfonic acids, for example of lignosulfonic acid (Borresperse® types, Borregaard, Norway), phenolsulfonic acid, naphthalenesulfonic acid (Morwet® types, Akzo Nobel, USA) and dibutylnaphthalenesulfonic acid (Nekal® types, BASF, Germany), and of fatty acids, alkyl- and alkylarylsulfonates, alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ethers, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin sulfite waste liquors and proteins, denatured proteins, polysaccharides (for example methylcellulose), hydrophobic-modified starches, polyvinyl alcohol (Mowiol® types, Clariant, Switzerland), polycarboxylates (Sokalan® types, BASF, Germany), polyalkoxylates, polyvinylamine (Lupamin® types, BASF, Germany), polyethyleneimine (Lupasol® types, BASF, Germany), polyvinylpyrrolidone and their copolymers.

Examples of thickeners (i.e. compounds which impart a modified flow behavior to the composition, i.e. high viscosity at rest and low viscosity in the agitated state) are polysaccharides and organic and inorganic layer minerals such as xanthan gum (Kelzan®, CP Kelco, USA), Rhodopol® 23 (Rhodia, France) or Veegum® (R.T. Vanderbilt, USA) or Attaclay® (Engelhard Corp., NJ, USA).

Bactericides may be added to stabilize the composition. Examples of bactericides are those based on dichlorophene and benzyl alcohol hemiformal (Proxel® from ICI or Acticide® RS from Thor Chemie and Kathon® MK from Rohm & Haas) and also isothiazolinone derivatives such as alkylisothiazolinones and benzisothiazolinones (Acticide® MBS from Thor Chemie). Examples of suitable antifreeze agents are ethylene glycol, propylene glycol, urea and glycerol. Examples of antifoams are silicone emulsions (such as, for example, Silikon® SRE, Wacker, Germany, or Rhodorsil®, Rhodia, France), long-chain alcohols, fatty acids, salts of fatty acids, organofluorine compounds and their mixtures. Examples of colorants are pigments, which are sparingly soluble in water, but also dyes, which are soluble in water. Examples of stickers are polyvinylpyrrolidone, polyvinyl acetate, polyvinyl alcohol and cellulose ethers (Tylose®, Shin-Etsu, Japan).

Examples of types of compositions are:

1. Types of Compositions for Dilution in Water
    i) Water-soluble concentrates (SL, LS)
        10 parts by weight of the active substances are dissolved in 90 parts by weight of water or a water-soluble solvent. Alternatively, wetters or other excipients are added. This gives a composition with an active substance content of 10% by weight.
    ii) Dispersible concentrates (DC)
        20 parts by weight of the active substances are dissolved in 70 parts by weight of cyclohexanone with addition of 10 parts by weight of a dispersant, for example polyvinylpyrrolidone. Upon dilution in water, a dispersion is obtained. The active substance content is 20% by weight.
    iii) Emulsifiable concentrates (EC)
        15 parts by weight of the active substances are dissolved in 75 parts by weight of xylene with addition of calcium dodecylbenzenesulfonate and castor oil ethoxylate (in each case 5 parts by weight). Upon dilution in water, an emulsion is obtained. The composition has an active substance content of 15% by weight.
    iv) Emulsions (EW, EO, ES)
        25 parts by weight of the active substances are dissolved in 35 parts by weight of xylene with addition of calcium dodecylbenzenesulfonate and castor oil ethoxylate (in each case 5 parts by weight). Using an emulsifier apparatus (for example Ultra-Turrax), this mixture is placed into 30 parts by weight of water and made into a homogeneous emulsion. Upon dilution in water, an emulsion is obtained. The composition has an active substance content of 25% by weight.
    v) Suspensions (SC, OD, FS)
        20 parts by weight of the active substances are comminuted in a stirred ball mill, with addition of 10 parts by weight of dispersants and wetters and 70 parts by weight of water or an organic solvent, to give a fine active substance suspension. Upon dilution in water, a stable suspension of the active substance is obtained. The active substance content in the composition is 20% by weight.
    vi) Water-dispersible and water-soluble granules (WG, SG)
        50 parts by weight of the active substances are ground finely, with addition of 50 parts by weight of dispersants and wetters, and prepared as water-dispersible or water-soluble granules by means of technical apparatuses (for example extrusion, spray tower, fluidized bed). Upon dilution in water, a stable dispersion or solution of the active substance results. The composition has an active substance content of 50% by weight.
    vii) Water-dispersible and water-soluble powders (WP, SP, SS, WS)
        75 parts by weight of the active substances are ground in a rotor-stator mill with addition of 25 parts by weight of dispersants and wetters and also silica gel. Upon dilution in water, a stable dispersion or solution of the active substance results. The active substance content of the composition is 75% by weight.
    viii) Gels (GF)
        In a ball mill, 20 parts by weight of the active substances, 10 parts by weight of dispersant, 1 part by weight of swelling agent and 70 parts by weight of water or of an organic solvent are ground to a fine suspension. Upon dilution with water, a stable suspension with an active substance content of 20% by weight is obtained.

2. Types of Compositions for Direct Application
    ix) Dusts (DP, DS)
        5 parts by weight of the active substances are ground finely and mixed intimately with 95 parts by weight of finely divided kaolin. This gives dust with an active substance content of 5% by weight.
    x) Granules (GR, FG, GG, MG)
        0.5 part by weight of the active substances are ground finely and combined with 99.5 parts by weight of carriers. Current methods in this context are extrusion, spray drying or the fluidized bed. This gives granules for direct application with an active substance content of 0.5% by weight.
    xi) ULV Solutions (UL)
        10 parts by weight of the active substances are dissolved in 90 parts by weight of an organic solvent, for example xylene. This gives a composition for direct application with an active substance content of 10% by weight.

The composition according to the invention is preferably in the form of an aqueous composition (such as SC), where the water-insoluble pesticide is present in the form of suspended particles. The water content may be at least 10% by weight, preferably at least 30% by weight. The suspended particles may be present in the form of crystalline or amorphous particles which are solid at 20° C. The suspended water-insoluble pesticide usually has a particle size distribution with an $x_{50}$ value of from 0.1 to 10 µm, preferably 0.2 µm to 5 µm and especially preferably 0.5 µm to 2 µm. The particle size distribution can be determined by laser light diffraction of an aqueous suspension comprising the particles. The sample preparation, for example the dilution to the measuring concentration, will, in this measuring method, depend on the fineness and concentration of the active substances in the suspension sample and on the apparatus used (for example Malvern Mastersizer), inter alia. The procedure must be developed for the system in question and is known to a person skilled in the art.

In another form the composition according to the invention is preferably any form except a gel. Gel may be understood as a dimensionally stable, readily deformable, liquid-rich and gas-rich, finely dispersed colloidal system of at least two components which for the most part comprise a solid colloidally dispersed substance with long or highly branched particles (gelling agent; also known as thickening agent or thickener) and a liquid (generally water) as dispersing agent. Gels can also be described as viscoelastic fluids; their fluid properties may lie between those of an ideal liquid and those of an ideal solid. The gels may be dimensionally stable, which can mean that they have a viscosity of at least 1000 mPa·s. The figures given for the viscosity in the context of the present invention refer to values as obtained using a Brookfield viscometer (1.5 rpm, Sp 63) at a temperature of 25 degrees centigrade. The composition according to the invention may have a viscosity of below 1000 mPas, preferably below 800, and in particular below 500 mPas.

A further subject matter is, therefore, seed comprising the composition according to the invention. To treat plant propagation materials, in particular seed, it is customary to use water-soluble concentrates (LS), suspensions (FS), dusts (DS), water-dispersible and water-soluble powders (WS, SS), emulsions (ES), emulsifiable concentrates (EC) and gels (GF). These compositions can be applied to the propagation materials, in particular seed, in undiluted or, preferably, diluted form. Here, the composition in question can be diluted 2- to 10-fold so that from 0.01 to 60% by weight, preferably from 0.1 to 40% by weight, of active substance are present in the compositions to be used for seed dressing. The application can be carried out before or during the sowing. The treatment of plant propagation material, in particular treatment of seed, is know to a person skilled in the art and is performed by dusting, coating, pelleting, dipping or immersing the plant propagation material, the treatment preferably being carried out by pelleting, coating and dusting or by the in-furrow treatment, so that for example premature germination of the seed is prevented. It is preferred to use suspensions for the seed treatment. Usually, such compositions comprise from 1 to 800 g/l active substance, from 1 to 200 g/l surfactants, from 0 to 200 g/l antifreeze agents, from 0 to 400 g/l binders, from 0 to 200 g/l colorants and solvents, preferably water.

The active substance concentrations in the ready-to-use preparations can be varied within substantial ranges. In general, they are between 0.0001 and 10%, preferably between 0.01 and 1%. The active substances can also be used successfully in the ultra-low-volume method (ULV), it being possible to apply compositions with more than 95% by weight of active substance, or indeed the active substance without additives. For use in plant protection, the application rates are between 0.001 and 2.0 kg of active substance per ha, preferably between 0.005 and 2 kg per ha, especially preferably between 0.05 and 0.9 kg per ha, in particular between 0.1 and 0.75 kg per ha, depending on the nature of the desired effect. When treating plant propagation materials, for example seed, amounts of active substance of from 0.1 to 1000 g/100 kg of propagation material or seed, preferably from 1 to 1000 g/100 kg, especially preferably from 1 to 100 g/100 kg, in particular from 5 to 100 g/100 kg, will generally be used. When used in the protection of materials or storage materials, the application rate of active substance depends on the nature of the field of application and on the desired effect. Conventional application rates in the protection of materials are, for example, from 0.001 g to 2 kg, preferably from 0.005 to 1 kg, of active substance per cubic meter of treated material.

Substances which may be admixed to the active substances or to the compositions comprising them are various types of oils, or wetters, adjuvants, herbicides, bactericides, other fungicides and/or pesticides, optionally also only just before use (tankmix). These agents can be admixed to the compositions according to the invention in the weight ratio 1:100 to 100:1, preferably 1:10 to 10:1. Adjuvants in this sense which are suitable are, in particular: organically modified polysiloxanes, for example Break Thru S 240®; alcohol alkoxylates, for example Atplus® 245, Atplus® MBA 1303, Plurafac® LF 300 and Lutensol® ON 30; EO-PO block polymers, for example Pluronic® RPE 2035 and Genapol® B; alcohol ethoxylates, for example Lutensol® XP 80; and sodium dioctylsulfosuccinate, for example Leophen® RA.

A further subject is a method of preparing the composition according to the invention by bringing the terpolymer and the agrochemical active substance into contact, for example by mixing. The abovementioned auxiliaries can optionally also be brought into contact with the composition. Further preparation methods for various types of compositions are as described above.

A further object is the use of the terpolymer for dispersing agrochemical active substances. The terpolymer is preferably used for suspending. Preferred agrochemical active substances are as described above.

The present invention furthermore relates to a method of controlling phytopathogenic fungi and/or undesirable vegetation and/or undesired insect or mite attack and/or for regulating the growth of plants, wherein the composition according to the invention is allowed to act on the respective pests, their environment or the crop plants to be protected from the respective pest, on the soil and/or on undesired plants and/or on the crop plants and/or on their environment. The term crop plants also includes those plants which have been modified by breeding, mutagenesis or recombinant methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such genetic modifications also comprise posttranslational modifications of proteins, oligo- or polypeptides, for example by means of glycosylation or binding of polymers such as, for example, prenylated, acetylated or farnesylated residues or PEG residues.

Advantages of the present invention are, inter alia, that it makes a high storage stability of the formulation possible; that the particle size growth of dispersed agrochemical active substances is slowed down or suppressed; that the agglomeration of dispersed agrochemical particles is slowed down or suppressed; that the settling of dispersed agrochemical active substances is slowed down or suppressed; that the abovementioned advantages are also attained in the presence of high salt concentrations.

The examples which follow illustrate the invention without imposing any limitation.

EXAMPLES

Surfactant A: Anionic surfactant, sodium salt of an alkyl-naphthalenesulfonic acid, water-soluble.
Surfactant B: Nonionic surfactant, alkylamine ethoxylate, water-soluble, surface tension (1 g/l water, room temperature) approximately 40 mN/m.

Example 1—Copolymer A

Initial charge: 216 g polyethylene glycol, average molar mass 35 000 g/mol
  216 g polyethylene glycol, average molar mass 1500 g/mol
  164 g propanol
  0.96 g triallylamine
  Feed 1: 384 g N-vinylformamide
  147.7 g diallyldimethylammonium chloride (DADMAC; 65% by weight form)
  164 g propanol
  Feed 2: 2.9 g tert-butyl peroctoate
  164 g propanol
  Feed 3: 420 g propanol
  Feed 4: 100 g propanol
  16 g sodium methoxide (30% by weight)

The homogenized initial charge was heated to 90° C. with nitrogen being passed through the system, and feed 1 was metered in over 4 hours, and 112 g of feed 2 over 5 hours.

After an hour of subsequent polymerization, 55 g of feed 2 were added and polymerization was continued for a further 1.5 hours. Then, using feed 3, dilution and cooling took place. Finally, the quantity of feed 3 was removed by distillation, feed 4 was added, the batch was heated under reflux for an hour, and the distillation was repeated. This gave copolymer A, containing N-vinylformamide and DADMAC in an 80/20 weight ratio. The molar mass Mw was 151 000 g/mol, with a PDI of 7.5. The solids content was 35% by weight (120° C., 2 hours), and the pH (in 10% form) was 4.5.

Example 2—Formulation 14 g of pyraclostrobin, 2 g of copolymer A from example 1, 2 g of surfactant A, 3.3 g of surfactant B, 13.1 g of glyphosate isopropylammonium salt (60% by weight in water), and 21.6 g of water were weighed into a vessel. 25 ml of glass beads (0.75-1.0 mm) were added, and an aqueous pyraclostrobin suspension was prepared by shaking on a laboratory shaker (4 h, 400 rpm). Thereafter, the glass beads were filtered off.

Example 3—Formulation (Comparative Experiment)

An aqueous suspension of pyraclostrobin was prepared as in example 2, the terpolymer of example 1 being replaced by
A) Atlox® 4915, or
B) Copolymer B (acrylic acid/AMPS 70/30).
Atlox® 4913 is a composition comprising 33% by weight of terpolymer (reaction product of methacrylic acid, methyl methacrylate and methoxypolyethylene glycol methacrylate), 33% by weight of propylene glycol, 1% by weight of xylene and 33% by weight of water), HLB value 11-12, commercially available from Uniquema.

The random copolymer B comprised the following monomers incorporated into the polymer: 70% by weight of acrylic acid and 30% by weight of the sodium salt of acrylamidopropanesulfonic acid (AMPS).

Example 4—Stability Test of the Suspension

The aqueous suspensions of examples 2, 3A and 3B were stored without agitation for 24 hours at room temperature and thereafter assessed visually with reference to a scale of from 1 (phase separation, no longer dispersible by shaking, clumpy) to 10 (no phase separation, highly viscous, readily dispersible).

TABLE 1

| Formulation of example | Stability assessment |
|---|---|
| 2 | 9 |
| 3A [a)] | 8 |
| 3B [a)] | 2 |

[a)] comparative experiment

We claim:
1. A composition comprising an agrochemical active substance and a copolymer which consists of 40 to 95% by weight of an N-vinylcarboxamide and 5 to 50% by weight of a diallyldialkylammonium salt incorporated into the polymer, based on the total amount of the copolymerized monomers, wherein the N-vinylcarboxamide is an N-vinyl-$C_1$-$C_{18}$-alkylcarboxamide and/or an N-vinyl-N—($C_1$-$C_{12}$-alkyl)-$C_1$-$C_{18}$-alkylcarboxamide; and wherein the diallyldialkylammonium salt corresponds to the formula (I)

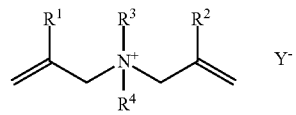

wherein $R^1$ and $R^2$ independently of each other are hydrogen or $C_1$-$C_4$-alkyl; $R^3$ and $R^4$ independently of each other are alkyl, hydroxyalkyl, carboxyalkyl, carboxyamidoalkyl or alkoxyalkyl having 1 to 18 carbon atoms; and $Y^-$ is an anion;
wherein the agrochemical active substance comprises a) a water-insoluble first pesticide and b) a water-soluble salt of a second pesticide or water-soluble inorganic fertilizer, wherein the copolymer is in dissolved form; the composition comprises at least 5% by weight of the second pesticide or of the inorganic fertilizer; the composition is in the form of an aqueous composition; the water-insoluble first pesticide is present in the form of suspended particles and has a solubility in water of up to 10 g/l at 20° C. and the water-soluble pesticide has a solubility of more than 10 g/l at 20° C.

2. The composition according to claim 1, comprising from 1 to 20% by weight of the copolymer.

3. The composition according to claim 1, wherein the copolymer is a random copolymer.

4. The composition according to claim 1, wherein the N-vinylcarboxamide is N-vinyl-N-methylformamide, N-vinylformamide, N-vinyl-N-ethylformamide, N-vinyl-N-propylformamide, N-vinyl-N-isopropylformamide, N-vinyl-N isobutylformamide, N-vinylacetamide, N-vinyl-N-methylacetamide, N-vinylpropionamide, or N-vinyl-N-methylpropionamide, and mixtures thereof.

5. A method of controlling phytopathogenic fungi and/or undesired plant growth and/or undesired insect or mite attack and/or for regulating the growth of plants, wherein the composition according to claim 1 is allowed to act on the respective pests, their environment or the crop plants to be protected from the respective pest, on the soil and/or on undesired plants and/or on the crop plants and/or on their environment.

6. The method of claim 5, wherein the composition comprises at least 5% by weight of the second pesticide or of the inorganic fertilizer.

7. The method of claim 5, wherein the composition is in the form of an aqueous composition, wherein the water-insoluble first pesticide is present in the form of suspended particles.

8. The method of claim 5, wherein the composition comprises from 1 to 20% by weight of the copolymer.

9. The method of claim 5, wherein the copolymer is a random copolymer.

10. The method of claim 5, where diallyldialkylammonium salt corresponds to the formula (I)

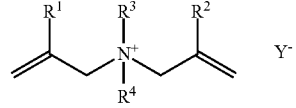

where $R^1$ and $R^2$ independently of each other are hydrogen or $C_1$-$C_4$-alkyl; $R^3$ and $R^4$ independently of each other are alkyl, hydroxyalkyl, carboxyalkyl, carboxyamidoalkyl or alkoxyalkyl having 1 to 18 carbon atoms; and $Y^-$ is an anion.

11. Seed treated with the composition according to claim 1.

12. The composition according to claim 1, wherein $R^1$ and $R^2$ independently of each other are hydrogen or methyl.

13. The composition according to claim 1, wherein $R^3$ and $R^4$ are methyl.

14. The composition according to claim 1, wherein the molecular weight of the polymer is from 5,000 g/mol to 250,000 g/mol.

15. The composition according to claim 1, wherein the co-polymer comprises 0.5% to 15% wt % of the composition.

16. The composition according to claim 1, wherein the N-vinylcarboxamide is N-vinylformamide.

* * * * *